(12) United States Patent
Saito et al.

(10) Patent No.: US 12,007,325 B2
(45) Date of Patent: Jun. 11, 2024

(54) ANALYSIS DEVICE AND ANALYSIS METHOD

(71) Applicant: JVCKENWOOD Corporation, Yokohama (JP)

(72) Inventors: Atsushi Saito, Yokohama (JP); Makoto Itonaga, Yokohama (JP)

(73) Assignee: JVCKENWOOD CORPORATION

( * ) Notice: Subject to any disclaimer, the term of this patent is extended or adjusted under 35 U.S.C. 154(b) by 355 days.

(21) Appl. No.: 17/477,685

(22) Filed: Sep. 17, 2021

(65) Prior Publication Data

US 2022/0003672 A1  Jan. 6, 2022

Related U.S. Application Data

(63) Continuation of application No. PCT/JP2020/010705, filed on Mar. 12, 2020.

(30) Foreign Application Priority Data

Mar. 25, 2019 (JP) .................................. 2019-056601

(51) Int. Cl.
G01N 21/55 (2014.01)
G01N 21/17 (2006.01)
G01N 33/53 (2006.01)

(52) U.S. Cl.
CPC .......... *G01N 21/55* (2013.01); *G01N 21/1717* (2013.01); *G01N 33/53* (2013.01); *G01N 2021/1791* (2013.01)

(58) Field of Classification Search
CPC .... G01N 21/55; G01N 21/1717; G01N 33/53; G01N 2021/1791; G01N 35/00029; G01N 21/253; B01L 9/56
USPC .......................................................... 356/432
See application file for complete search history.

(56) References Cited

U.S. PATENT DOCUMENTS

2018/0238790 A1  8/2018  Iwama et al.
2018/0321227 A1  11/2018  Iwama et al.

FOREIGN PATENT DOCUMENTS

| EP | 3358349 A1 | 8/2018 |
| EP | 3413047 A1 | 12/2018 |
| JP | 201758242 A | 3/2017 |
| JP | 2018136297 A | 8/2018 |
| WO | 2017134944 A1 | 8/2017 |
| WO | 2018135404 A1 | 7/2018 |

OTHER PUBLICATIONS

Extended European Search Report dated May 9, 2022 for application No. EP20777591.7.

*Primary Examiner* — Md M Rahman
(74) *Attorney, Agent, or Firm* — Nath, Goldberg & Meyer; Jerald L. Meyer

(57) ABSTRACT

A signal processing circuit uses gate signals corresponding to a plurality of divided measurement ranges to extract a fine particle pulse signal from a light reception level signal generated by an optical pickup, count the pulse number for each of the gate signals, and output a count value for each of the divided measurement ranges. A count value in-plane distribution generating unit generates count value in-plane distribution data in a measurement range based on the count value. A reaction region position coordinate computation unit estimates positions of all reaction regions from the count value in-plane distribution data. A reaction region count value computation unit calculates the count values for each of all the estimated reaction regions.

4 Claims, 8 Drawing Sheets

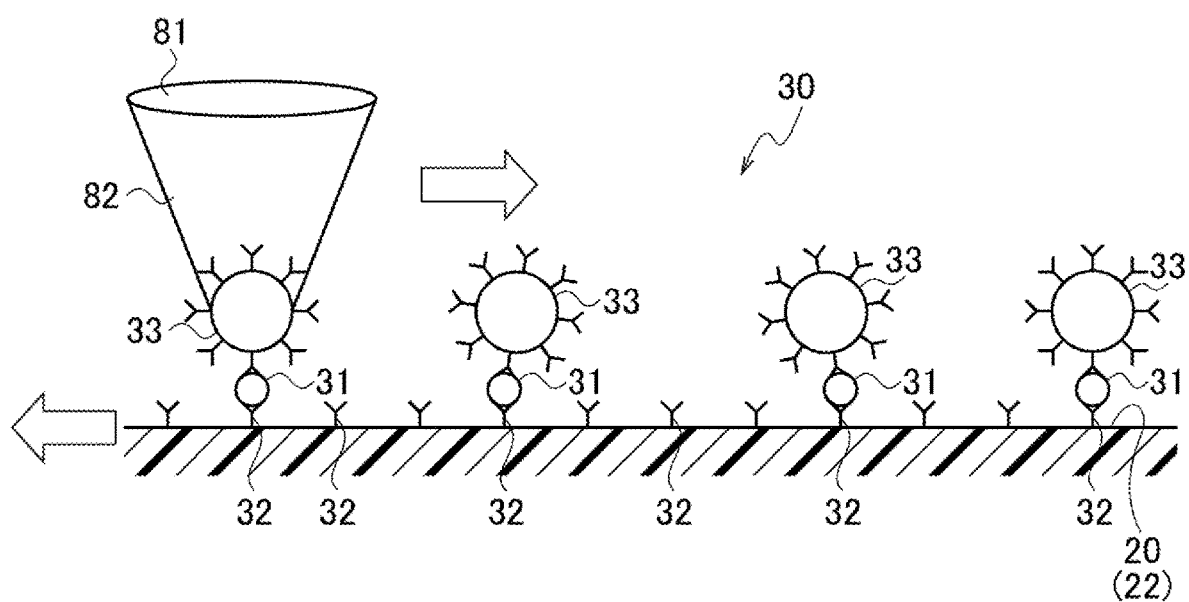

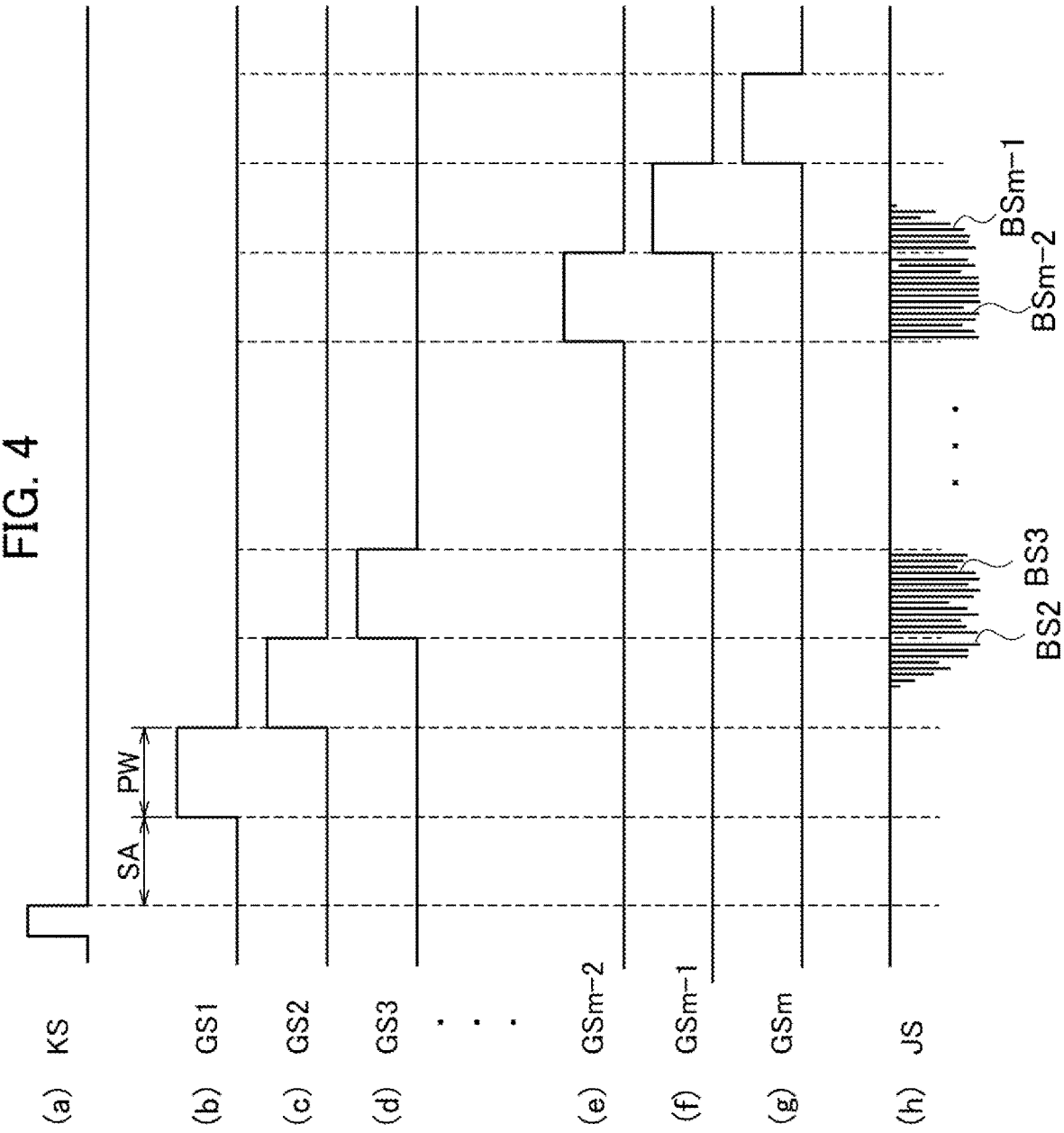

FIG. 6

| MEASUREMENT GATE SIGNAL | MEASUREMENT RANGE RM ↙ TCD | | | | | | | | | | |
|---|---|---|---|---|---|---|---|---|---|---|---|
| TRACK | GS1 | GS2 | GS3 | GS4 | GS5 | ... | GSm-4 | GSm-3 | GSm-2 | GSm-1 | GSm |
| TR1 | 0 | 0 | 0 | 0 | 0 | ... | 0 | 0 | 0 | 0 | 0 |
| TR2 | 0 | 0 | 0 | 0 | 10 | ... | 10 | 0 | 0 | 0 | 0 |
| TR3 | 0 | 0 | 10 | 10 | 50 | ... | 100 | 50 | 10 | 0 | 0 |
| TR4 | 0 | 0 | 50 | 50 | 100 | ... | 100 | 100 | 50 | 0 | 0 |
| TR5 | 0 | 10 | 100 | 100 | 100 | ... | 100 | 100 | 50 | 10 | 0 |
| TR6 | 0 | 10 | 100 | 100 | 100 | ... | 100 | 100 | 100 | 10 | 0 |
| TR7 | 0 | 50 | 100 | 100 | 100 | ... | 100 | 100 | 100 | 10 | 0 |
| TR8 | 0 | 50 | 100 | 100 | 100 | ... | 100 | 100 | 100 | 10 | 0 |
| TR9 | 0 | 50 | 100 | 100 | 100 | ... | 100 | 100 | 100 | 10 | 0 |
| ... | ... | ... | ... | ... | ... | | ... | ... | ... | ... | ... |
| TRn-8 | 0 | 10 | 100 | 100 | 100 | ... | 100 | 100 | 100 | 10 | 0 |
| TRn-7 | 0 | 10 | 100 | 100 | 100 | ... | 100 | 100 | 100 | 10 | 0 |
| TRn-6 | 0 | 10 | 50 | 100 | 100 | ... | 100 | 100 | 100 | 10 | 0 |
| TRn-5 | 0 | 10 | 50 | 100 | 100 | ... | 100 | 100 | 10 | 0 | 0 |
| TRn-4 | 0 | 0 | 50 | 100 | 100 | ... | 100 | 100 | 0 | 0 | 0 |
| TRn-3 | 0 | 0 | 10 | 50 | 50 | ... | 100 | 50 | 0 | 0 | 0 |
| TRn-2 | 0 | 0 | 0 | 10 | 10 | ... | 50 | 10 | 0 | 0 | 0 |
| TRn-1 | 0 | 0 | 0 | 0 | 0 | ... | 10 | 0 | 0 | 0 | 0 |
| TRn | 0 | 0 | 0 | 0 | 0 | ... | 0 | 0 | 0 | 0 | 0 |

ANALYSIS DEVICE AND ANALYSIS METHOD

CROSS REFERENCE TO RELATED APPLICATION

This application is a Continuation of PCT Application No. PCT/JP2020/010705, filed on Mar. 12, 2020, and claims the priority of Japanese Patent Application No. 2019-056601, filed Mar. 25, 2019, the entire contents of both of which are incorporated herein by reference.

BACKGROUND

The present disclosure relates to an analysis device and an analysis method for analyzing biological materials such as antigens or antibodies.

Immunoassays are known which are for quantitatively analyzing discovery of diseases, effects of medical treatment, and the like by detecting particular antigens or antibodies associated with the disease as biomarkers.

A specimen detection unit disclosed in Japanese Unexamined Patent Application Publication No. 2017-58242 includes a plurality of wells as reaction regions, and the plurality of wells are formed from a cartridge having a plurality of through-holes and an analysis substrate. Japanese Unexamined Patent Application Publication No. 2017-58242 discloses that a measurement range is set in advance on the analysis substrate, the measurement range being a range in which an analysis device counts fine particles. Japanese Unexamined Patent Application Publication No. 2017-58242 also discloses that the well is formed at a position where the measurement range and the through-hole coincide with each other.

Further, the following is described as an analysis method using the above described specimen detection unit. First, a buffer solution containing the antibody is injected into the well to fix the antibody on the analysis substrate, and then the inside of the well is washed and dried. Next, a sample solution containing a detection target substance is injected into the well, and the detection target substance is bound with the antibody, and then the inside of the well is washed and dried. Further, a buffer solution containing fine particles to be bound with the detection target substance is injected into the well, and the fine particles are bound with the detection target substance. Then, a reaction region is formed in which the detection target substance is captured by the antibody and the fine particle s. The cartridge is removed from the specimen detection unit formed with the reaction regions. The analysis substrate from which the cartridge is removed is placed in the analysis device, and the fine particles detected from the measurement range are counted to indirectly quantify the detection target substance.

SUMMARY

However, depending on the alignment accuracy of the well and the analysis substrate or the like, the reaction region may be formed at a position deviated from a preset measurement range on the analysis substrate. If the reaction region is deviated from the measurement range, the quantitative determination of the fine particles in the measurement range may not be performed with high accuracy, and this causes the deterioration in the analysis accuracy.

As a countermeasure, suppose that the measurement range is set to be smaller than the reaction region, so that the reaction region is not deviated from the measurement range by considering the deviation amount of the reaction region. In the above case, if a variation occurs in a binding state between the antibody and the detection target substance, or a binding state between the detection target substance and the fine particles in the reaction region, a region with a large count value, and a region with a small count value are mixed together. Accordingly, the in-plane distribution of the count values occurs, and this causes the deterioration in the analysis accuracy.

An object of an embodiment of the present invention is to provide an analysis device and an analysis method capable of accurately quantifying fine particles, even if a reaction region is formed at a position deviated from a measurement range present on an analysis substrate, and suppressing the deterioration in the analysis accuracy.

A first aspect of an embodiment of the present invention provides an analysis device using an analysis substrate on which a plurality of reaction regions are formed by a fine particle for labeling a detection target substance being fixed to the detection target substance captured on a track. The analysis device includes an optical pickup that receives reflected light obtained by irradiating the analysis substrate with a laser beam, and generates a light reception level signal, a signal processing circuit that generates gate signals for each of a plurality of the tracks within a measurement range preset on the analysis substrate, the gate signals corresponding to a plurality of divided measurement ranges obtained by dividing each of the tracks in a circumferential direction, extracts a fine particle pulse signal from the light reception level signal by using the gate signals, counts a pulse number for each of the gate signals from the extracted fine particle pulse signals, and outputs a count value for each of the divided measurement ranges, a count value in-plane distribution generating unit that generates count value in-plane distribution data in the measurement range, based on the count value output from the signal processing circuit, a reaction region position coordinate computation unit that estimates positions of all the reaction regions, based on the count value in-plane distribution data, and a reaction region count value computation unit that calculates the count value for each of all the estimated reaction regions.

A second aspect of an embodiment of the present invention provides an analysis method including receiving, by an optical pickup, reflected light obtained by irradiating an analysis substrate with a laser beam, and generating a light reception level signal, the analysis substrate being formed with a plurality of reaction regions by a fine particle for labeling a detection target substance being fixed to the detection target substance captured on a track, generating, by a signal processing circuit, gate signals for each of a plurality of the tracks within a measurement range preset on the analysis substrate, the gate signals corresponding to a plurality of divided measurement ranges obtained by dividing each of the tracks in a circumferential direction, extracting a fine particle pulse signal from the light reception level signal by using the gate signals, counting a pulse number for each of the gate signals from the extracted fine particle pulse signal, and outputting a count value for each of the divided measurement ranges, and generating, by a count value in-plane distribution generating unit, count value in-plane distribution data in the measurement range based on the count value output from the signal processing circuit, estimating, by a reaction region position coordinate computation unit, positions of all the reaction regions based on the count value in-plane distribution data, and calculating, by a reaction region count value computation unit, the count value for all the estimated reaction regions.

According to an analysis device and an analysis method of an embodiment, even if a reaction region is formed at a position deviated from a target position on an analysis substrate, fine particles can be quantified accurately, and the deterioration in the analysis accuracy can be suppressed.

BRIEF DESCRIPTION OF THE DRAWINGS

FIG. 2 is a diagram schematically showing a state in which in a reaction region, a detection target substance is captured on an analysis substrate by antibodies and fine particles in a sandwiched manner.

FIG. 4 is a diagram showing an example of the relationship among a reference position detection signal, a measurement gate signal, a light reception level signal, and a fine particle pulse signal.

FIG. 6 is a diagram showing an example of table format count data.

DETAILED DESCRIPTION

Figure 1:
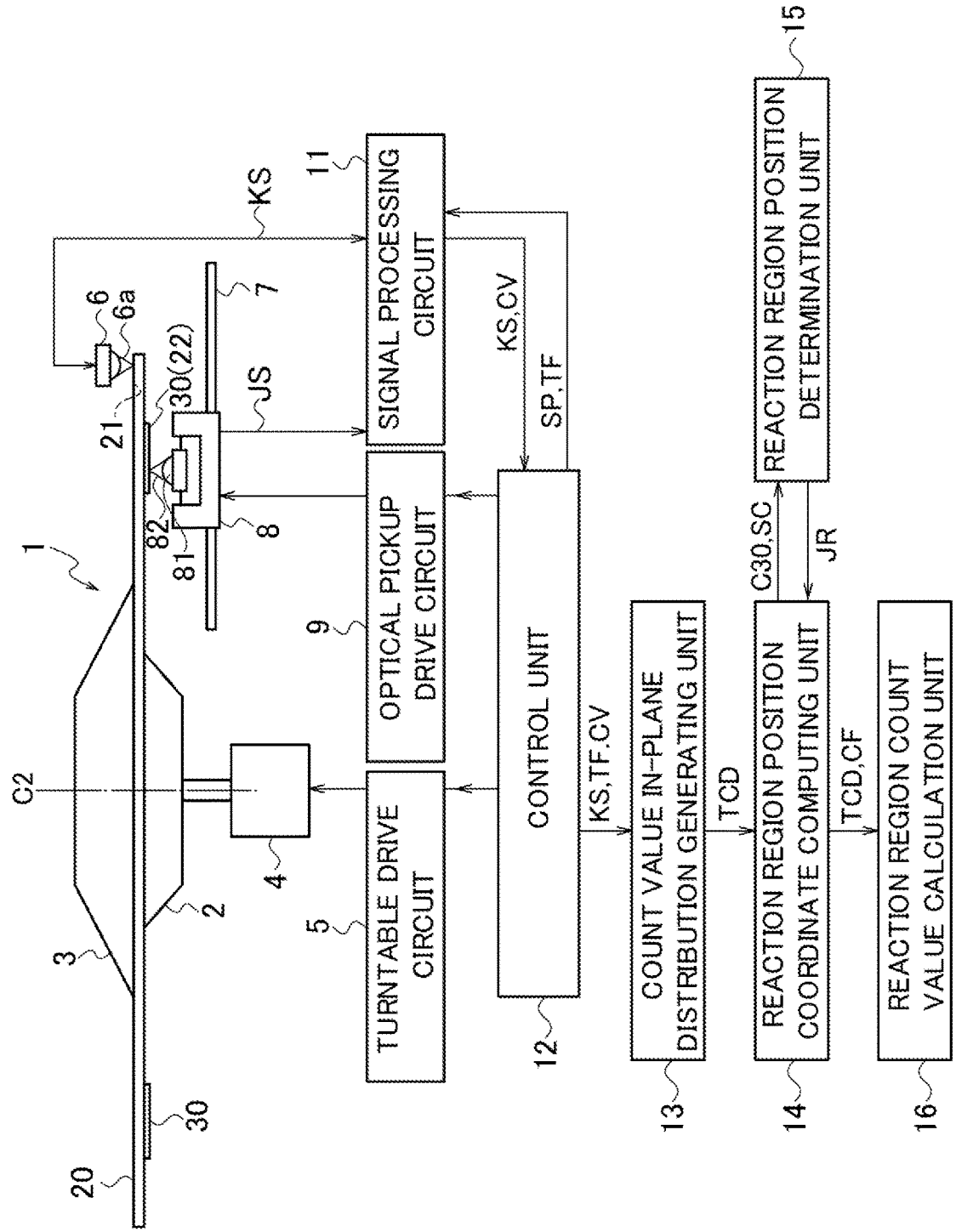
FIG. 1 is a configuration diagram showing an example of an analysis device of an embodiment.

With reference to FIG. 1, a configuration example of an analysis device according to an embodiment will be described. An analysis device 1 includes a turntable 2, a clamper 3, a turntable drive unit 4, a turntable drive circuit 5, a reference position detection sensor 6, a guide shaft 7, an optical pickup 8, and an optical pickup drive circuit 9. Further, the analysis device 1 includes a signal processing circuit 11, a control unit 12, a count value in-plane distribution generating unit 13, a reaction region position coordinate computation unit 14, a reaction region position determination unit 15, and a reaction region count value computation unit 16. A computing device or a CPU (Central Processing Unit) may be used as the signal processing circuit 11, the control unit 12, the count value in-plane distribution generating unit 13, the reaction region position coordinate computation unit 14, the reaction region position determination unit 15, and the reaction region count value computation unit 16.

A plurality of reaction regions 30 are formed on an analysis substrate 20. The analysis substrate 20 is placed on the turntable 2 such that the reaction regions 30 face downward. The analysis substrate 20 is, for example, an optical disk having a disc shape. The clamper 3 is driven in a direction away from and close to the turntable 2. The analysis substrate 20 is held by the clamper 3 and the turntable 2.

The turntable drive unit 4 rotationally drives the turntable 2 around a rotation axis C2 together with the analysis substrate 20 and the clamper 3. A spindle motor may be used as the turntable drive unit 4. The turntable drive circuit 5 controls the turntable drive unit 4. For example, the turntable drive circuit 5 controls the turntable drive unit 4, such that the turntable 2 rotates at a constant linear velocity together with the analysis substrate 20 and the clamper 3.

The reference position detection sensor 6 is disposed in the vicinity of an outer peripheral portion of the analysis substrate 20. The reference position detection sensor 6 is, for example, an optical sensor such as a photoreflector. The reference position detection sensor 6 irradiates, with detecting light 6a, the outer peripheral portion of the rotating analysis substrate 20. Then, reference position detection sensor 6 receives reflected light from the analysis substrate 20.

The reference position detection sensor 6 detects a notch 21 of the analysis substrate 20, and generates a reference position detection signal KS to outputs the signal to the signal processing circuit 11. The reference position detection signal KS is, for example, a pulse signal that rises and is in an ON state when the notch 21 reaches a position detected by the reference position detection sensor 6, that is, a position irradiated with the detection light 6a. Alternatively, the reference position detection signal KS falls and is in an OFF state when the notch 21 passes the position.

In other words, the reference position detection sensor 6 detects a reference position for each rotation cycle and track of the analysis substrate 20. A transmission type optical sensor may be used as the reference position detection sensor 6. In this case, the reference position detection sensor 6 irradiates, with the detection light 6a, the analysis substrate 20. Then, the reference position detection sensor 6 receives the detection light 6a passing the notch 21 to detect the reference position for each rotation cycle and track of the analysis substrate 20.

The guide shaft 7 is disposed parallel to the analysis substrate 20, and along a radial direction of the analysis substrate 20. The optical pickup 8 is supported by the guide shaft 7. The optical pickup 8 has an objective lens 81. The optical pickup drive circuit 9 controls driving of the optical pickup 8. The optical pickup drive circuit 9 moves the optical pickup 8 along the guide shaft 7, and moves the objective lens 81 of the optical pickup 8 in the vertical direction. The optical pickup 8 is driven along the guide shaft 7, in a direction orthogonal to the rotation axis C2 of the turntable 2, in the radial direction of the analysis substrate 20, and in parallel with the analysis substrate 20.

The optical pickup 8 irradiates the analysis substrate 20 with a laser beam 82. The laser beam 82 is condensed by the objective lens 81 to a track region 22 where the reaction regions 30 on the analysis substrate 20 are formed. While the analysis substrate 20 is rotated, the optical pickup 8 is driven in the radial direction of the analysis substrate 20. The optical pickup 8 receives the reflected light from the analysis substrate 20. The optical pickup 8 detects a light reception level of the reflected light to generate a light reception level signal JS, and outputs the generated signal to the signal processing circuit 11.

The control unit 12 controls the turntable drive circuit 5, the optical pickup drive circuit 9, and the signal processing circuit 11. The control unit 12 controls the turntable drive circuit 5 to rotate the turntable 2, for example, at a constant linear velocity, or stop the turntable 2. The control unit 12 controls the optical pickup drive circuit 9 to move the optical pickup 8 to a target position in the radial direction of the analysis substrate 20. The control unit 12 further controls the circuit to adjust a vertical position of the objective lens 81 so that the laser beam 82 is condensed in the track region 22.

The control unit 12 outputs a measurement parameter SP to the signal processing circuit 11. The measurement parameter SP is a measurement parameter for generating a plurality of measurement gate signals GS. Further, the measurement parameter SP includes pieces of measurement information such as the number of reaction regions 30, a time corresponding to the distance from the notch 21 to each of the reaction regions 30, and the timing and gate width of the measurement gate signals GS in each track. The signal processing circuit 11 is, for example, a counter. Processes of the count value in-plane distribution generating unit 13, the reaction region position coordinate computation unit 14, the reaction region position determination unit 15, and the reaction region count value computation unit 16 will be described later.

FIG. 2 shows a state in which the analysis substrate 20 shown in FIG. 1 is turned upside down. A plurality of antibodies 32 binding with a specific antigen of a detection target substance 31 are fixed on the analysis substrate 20 on the reaction regions 30. The detection target substance 31 is bound with the antibodies 32 to be fixed on the analysis substrate 20. A plurality of antibodies binding with a specific antigen of the detection target substance 31 are fixed on surfaces of fine particles 33 for labeling the detection target substance 31. The fine particles 33 are specifically bound with the detection target substance 31 to be captured on the analysis substrate 20. Therefore, the detection target substance 31 is captured on the track of the analysis substrate 20 by the antibodies 32 and the fine particles 33 in a sandwiched manner. The detection target substance 31 is, for example, an exosome.

An example of an analysis method of an embodiment will be described with reference to flowcharts shown in FIGS. 3A and 3B, and FIGS. 4 to 7. In step S1 of FIG. 3A, the control unit 12 controls the turntable drive circuit 5 such that the analysis substrate 20 rotates, for example, at a constant linear velocity. The control unit 12 causes the turntable drive unit 4 to rotationally drive the turntable 2.

In step S2, the control unit 12 causes the reference position detection sensor 6 to irradiate the analysis substrate 20 with the detection light 6a. In step S3, the control unit 12 causes the optical pickup 8 to irradiate the analysis substrate 20 with the laser beam 82. The control unit 12 may perform step S3 after step S2, or alternatively perform step S2 after step S3, or may perform step S2 and step S3 at the same time.

In step S4, the control unit 12 controls the optical pickup drive circuit 9 to move the optical pickup 8 so that a target track of the analysis substrate 20 is irradiated with the laser beam 82. In step S5, the reference position detection sensor 6 generates the reference position detection signal KS by detecting the notch 21, and outputs the generated signal to the signal processing circuit 11.

In step S6, the optical pickup 8 receives the reflected light from the analysis substrate 20. The optical pickup 8 detects the light reception level of the reflected light to generate the light reception level signal JS (a first detection signal), and outputs the generated signal to the signal processing circuit 11. In step S7, the control unit 12 outputs the measurement parameter SP to the signal processing circuit 11.

The signal processing circuit 11 acquires the reference position detection signal KS from the reference position detection sensor 6, and acquires the light reception level signal JS from the optical pickup 8. Further, the signal processing circuit 11 acquires the measurement parameter SP and track information TF from the control unit 12. The track information TF includes information on a target track (a track to be measured) irradiated with the laser beam 82 in step S4 above (for example, information such as track number or track position).

In step S8 of FIG. 4, the signal processing circuit 11 acquires a phase SA in the track to be measured TR based on the reference position detection signal KS and the track information TF. The phase SA is preset for each track. The signal processing circuit 11 may include a storage unit that stores the phase SA set for each track as table format data. The signal processing circuit 11 can recognize the track number or track position of a currently measured track from the track information TF, and acquire the phase SA corresponding to the track.

The signal processing circuit 11 generates the plurality of measurement gate signals GS based on the reference position detection signal KS, the phase SA, and the measurement parameter SP. In FIG. 4, (a) shows the reference position detection signal KS in a track TR, (b) to (g) show a plurality of measurement gate signals GS1 to GSm in the track TR, and (h) shows the light reception level signal JS in the track TR.

For example, the signal processing circuit 11 generates, in the currently measured track, a measurement gate signal GS1 which rises at a time point after the phase SA, which phase starts when the reference position detection signal KS falls, based on the measurement parameter SP. Further, the signal processing circuit 11 generates a measurement gate signal GS2 which rises when the measurement gate signal GS1 falls. In this manner, the signal processing circuit 11 generates the plurality of measurement gate signals GS in the currently measured track. Further, the signal processing circuit 11 generates the plurality of measurement gate signals GS for each track based on the reference position detection signal KS, the phase SA, and the measurement parameter SP in each track. In other words, the signal processing circuit 11 generates gate signals GS for each of the plurality of tracks TR within the measurement range RM, the gate signals GS corresponding to a plurality of divided measurement ranges obtained by dividing each of the tracks in the circumferential direction.

Figure 5:
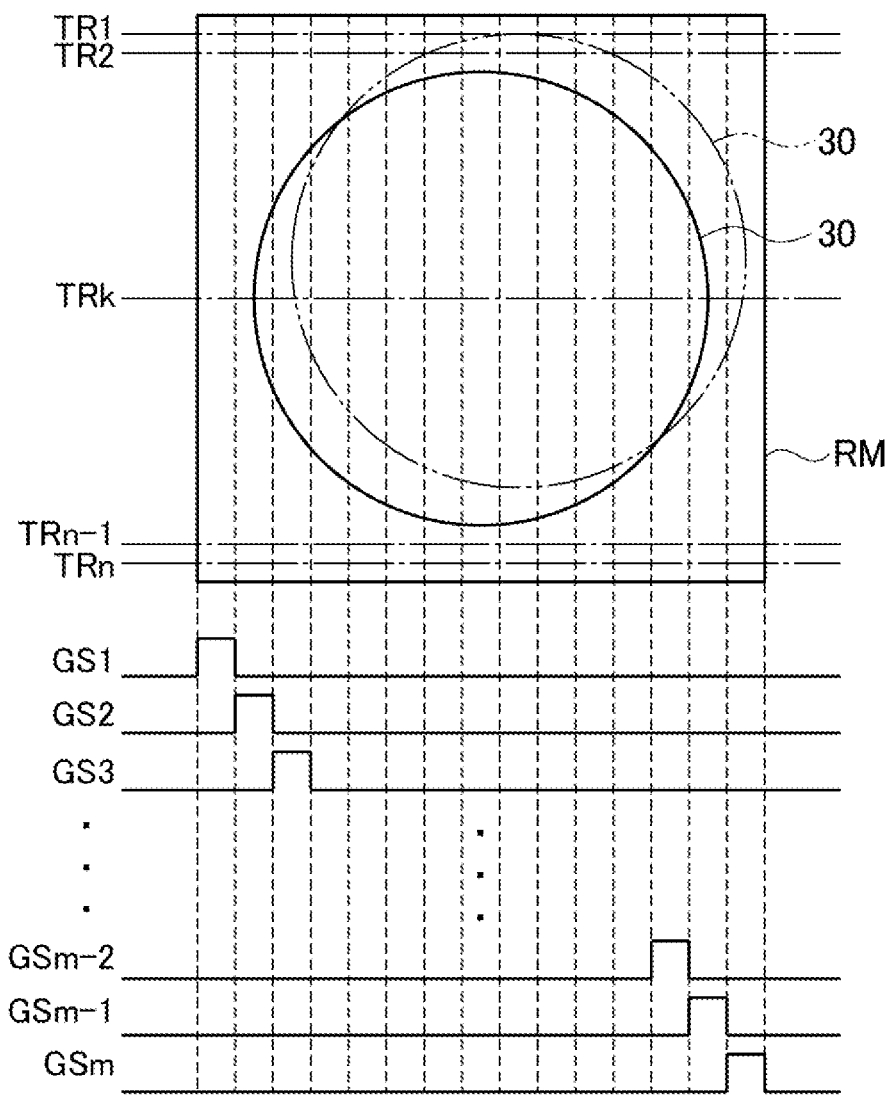
FIG. 5 is a diagram showing an example of the relationship among a reaction region, a measurement range, a track, and a measurement gate signal.

FIG. 5 shows the positional relationship among the reaction regions 30, the measurement range RM by the measurement gate signals GS1 to GSm, and tracks to be measured TR1 to TRn. In FIG. 5, the reaction region 30 formed at a target position on the analysis substrate 20 is shown by a solid line, and the reaction region 30 formed at a position which is deviated from the target position is shown by a two-dot chain line. Even if the reaction region 30 is formed at the position which is deviated from the target position, the measurement range RM is preferably set to be larger than the reaction regions 30, so that the reaction region 30 is positioned within the measurement range RM.

In step S9, the signal processing circuit 11 extracts fine particle pulse signals BS1 to BSm (second detection signals) from the light reception level signal JS output from the optical pickup 8 for each of the measurement gate signals GS1 to GSm of all tracks TR1 to TRn, and counts the pulse number for each of the fine particle pulse signals BS1 to BSm. Accordingly, a count value CV for each of the measurement gate signals GS1 to GSm of all the tracks TR1 to TRn is acquired. In other words, the signal processing circuit 11 counts the fine particles 33 for each measurement gate signal GS, the fine particles 33 being specifically bound with the detection target substance 31 captured in the reaction regions 30. FIG. 4(h) shows an example of the fine particle pulse signals BS1 to BSm in a track TRk shown in FIG. 5.

In step S10, the count value in-plane distribution generating unit 13 acquires the reference position detection signal KS, the track information TF, and a count value CV from the signal processing circuit 11 via the control unit 12. Then, the count value in-plane distribution generating unit 13 generates, in step S10, count value in-plane distribution data in the measurement range RM as table format count data TCD. Hereinafter, the table format count data TCD is simply referred to as table data TCD.

FIG. 6 shows an example of the table data TCD. Each numerical value in FIG. 6 shows an example of the count value CV of the pulse number in the fine particle pulse signal BS for each of the measurement gate signals GS1 to GSm of the tracks TR1 to TRn in the measurement range RM. In FIG. 6, the count value CV is indicated by a numerical value of 10, 50, or 100, but in an actual case, an actual count value is input. In other words, in the reaction regions 30, the pulse number in the fine particle pulse signal BS is counted for each of the plurality of divided measurement ranges, the divided measurement ranges being obtained by dividing each of the plurality of tracks TR in the measurement range RM in the circumferential direction.

In step S11, the reaction region position coordinate computation unit 14 acquires the table data TCD from the count value in-plane distribution generating unit 13. Further, the reaction region position coordinate computation unit 14 acquires the in-plane distribution of the count values from the table data TCD, and estimates the position of the reaction region 30 (for example, the central coordinate of the reaction region 30). The reaction region position coordinate computation unit 14 estimates the position of the reaction region 30 from the total value of the count value CV included in a shape of a predetermined size based on count value in-plane distribution data.

If the reaction region 30 is set as a circle having a predetermined radius, the reaction region position coordinate computation unit 14 may specify a region corresponding to the above described circle by processing the in-plane distribution of the count values in the table data TCD as an image, and may estimate the central coordinate of the reaction region 30 from the center position of the circle. The reaction region position coordinate computation unit 14 may estimate the position (range) of the reaction region 30 from the predetermined radius and the central coordinate. The reaction region position coordinate computation unit 14 may scan the circle that corresponds to the reaction region 30 on the table data TCD, and may set the center position (center) of the circle at which the sum of the count values in the circle becomes maximum, as the position (the central coordinate) of the reaction region 30.

The reaction region position coordinate computation unit 14 may acquire a score SC indicating the degree of accuracy of detection from the in-plane distribution of the count values. The score SC is an index generally used in image recognition, and indicates the degree of coincidence between a figure obtained from the in-plane distribution and the circle having the predetermined radius. The higher the degree of coincidence, the higher the value of the score SC.

The control unit 12, the reference position detection sensor 6, the optical pickup 8, the signal processing circuit 11, the count value in-plane distribution generating unit 13, or the reaction region position coordinate computation unit 14 performs the processes of steps S4 to S11 for all the reaction regions 30. Accordingly, the reaction region position coordinate computation unit 14 estimates the positions (central coordinates) of all the reaction regions 30 and acquires the score SC.

In step S12, the reaction region position determination unit 15 acquires, from the reaction region position coordinate computation unit 14, the estimated positions (the central coordinates) of all the reaction regions 30 and the score SC. Further, the reaction region position determination unit 15 determines at least either one of the position (the central coordinate) of the reaction region 30 and the score SC, and selects the reference reaction region 30 (a first reaction region) based on the determination result. The number of the first reaction regions selected by the reaction region position determination unit 15 is two or three.

The reaction region position determination unit 15 may determine, for example, whether a central coordinate C30 is located within a predetermined region for all the reaction regions 30, and select the reaction regions 30 whose central coordinate is located within the predetermined region, as the reference reaction region 30.

The reaction region position determination unit 15 may determine, for example, whether the score SC is a threshold value or more for all the reaction regions 30, and select the reaction regions 30 in which the score SC is the threshold value or more, as the reference reaction region 30. The reaction region position determination unit 15 may select, as the reference reaction region 30, for example, the reaction regions 30 in which the difference between count values of the successive gate signals GS is larger than the threshold value.

An operator may check the in-plane distribution of the count values and select the reference reaction region 30 through a GUI (Graphical User Interface) or the like. In order to determine a circle CE with high accuracy which will be described later, it is preferable to select a plurality of reaction regions 30 located at positions distant from one another as the reference reaction regions 30.

Figure 7:
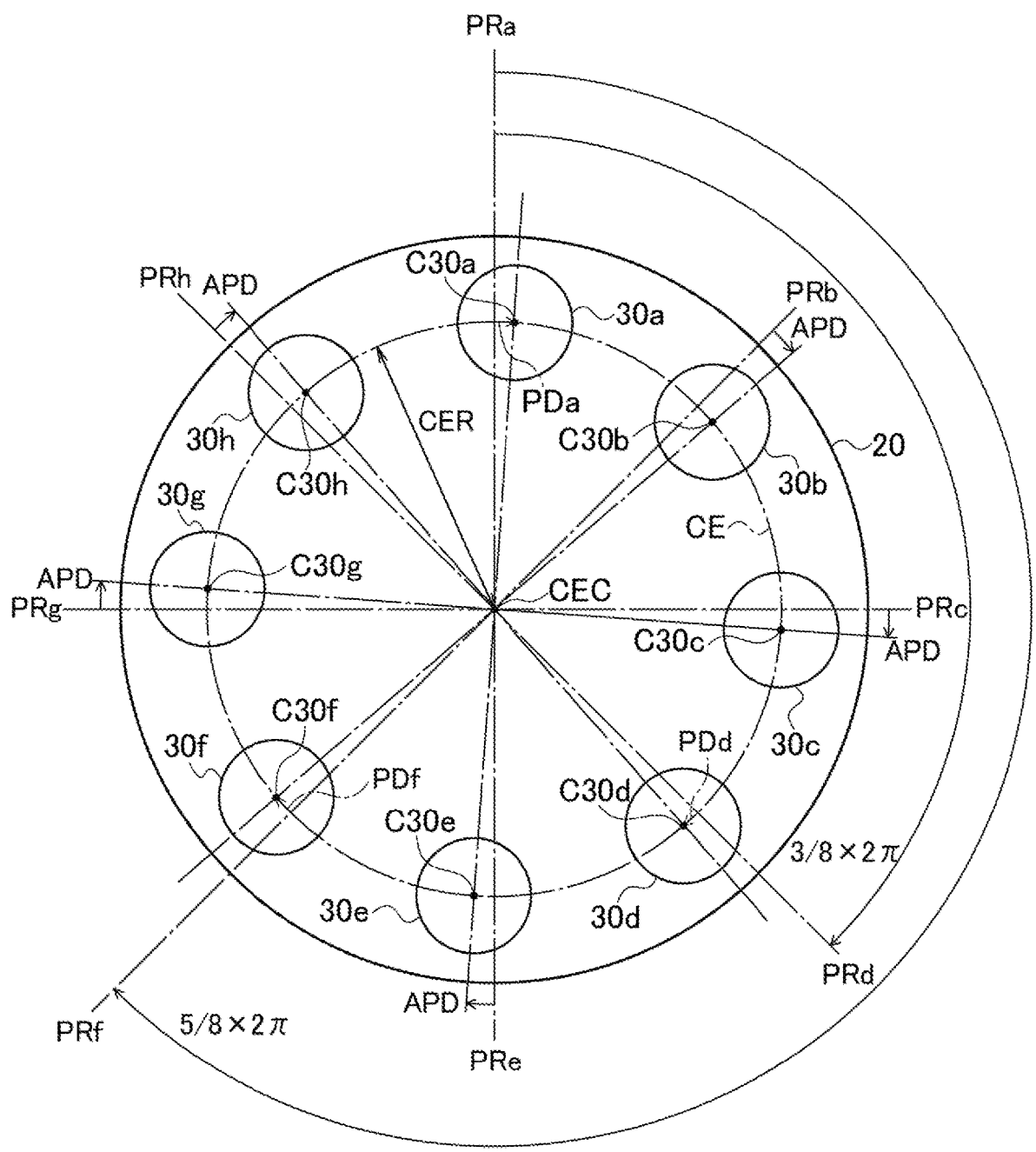
FIG. 7 is a diagram showing an example of the relationship among a reaction region, a phase reference, and a rotation phase error.

FIG. 7 shows a state in which eight reaction regions 30 are formed on the analysis substrate 20 at equal intervals on the same circumference. FIG. 7 shows the eight reaction regions 30 as reaction regions 30a to 30h for the purpose of distinction. A case will be described below in which the reaction region position determination unit 15 selects the three reaction regions 30a, 30d, and 30f shown in FIG. 7 as the reference reaction regions 30 in step S12.

Figure 3A:
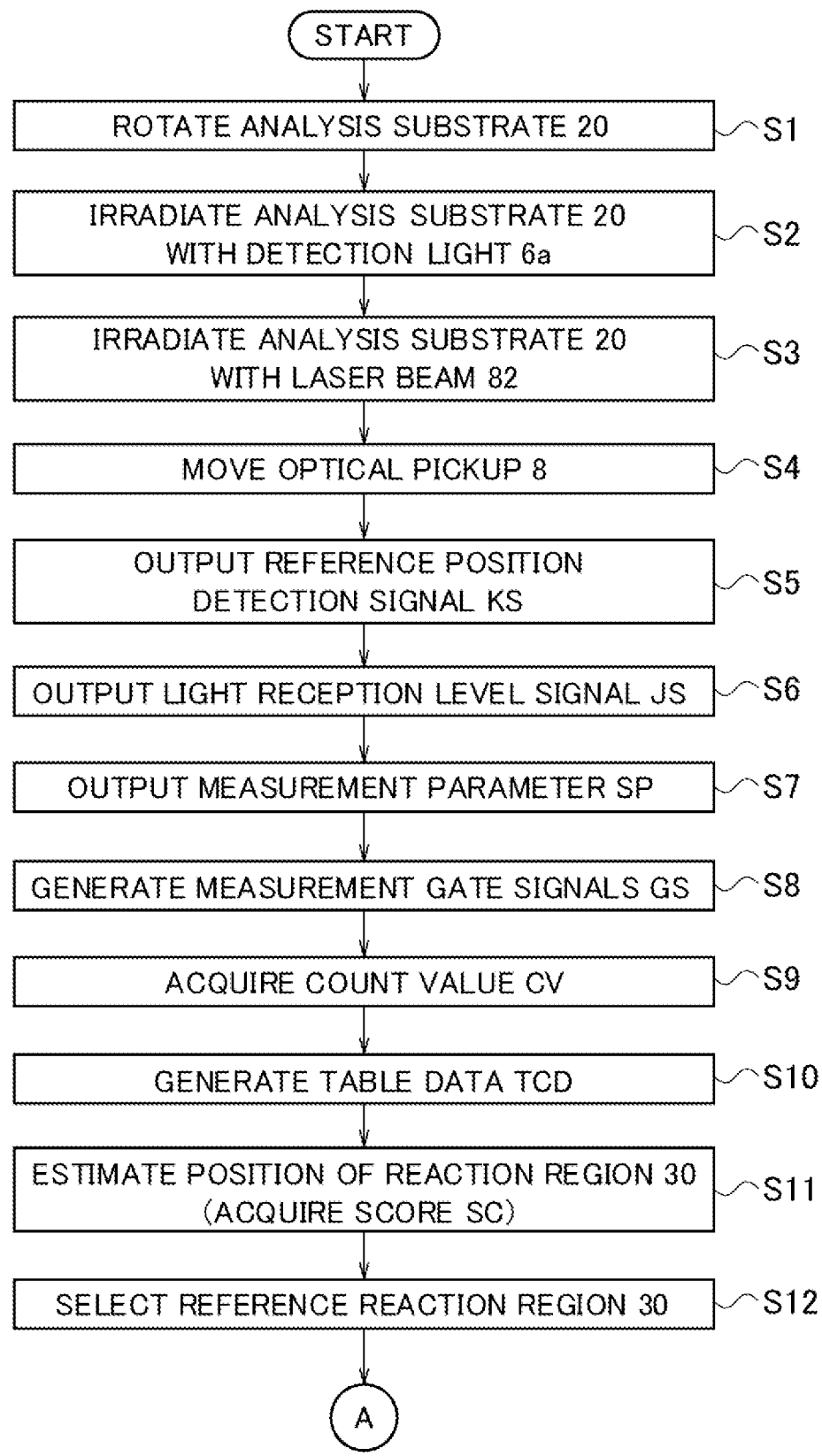
FIG. 3A is a flowchart showing an example of an analysis method of an embodiment.
Figure 3B:
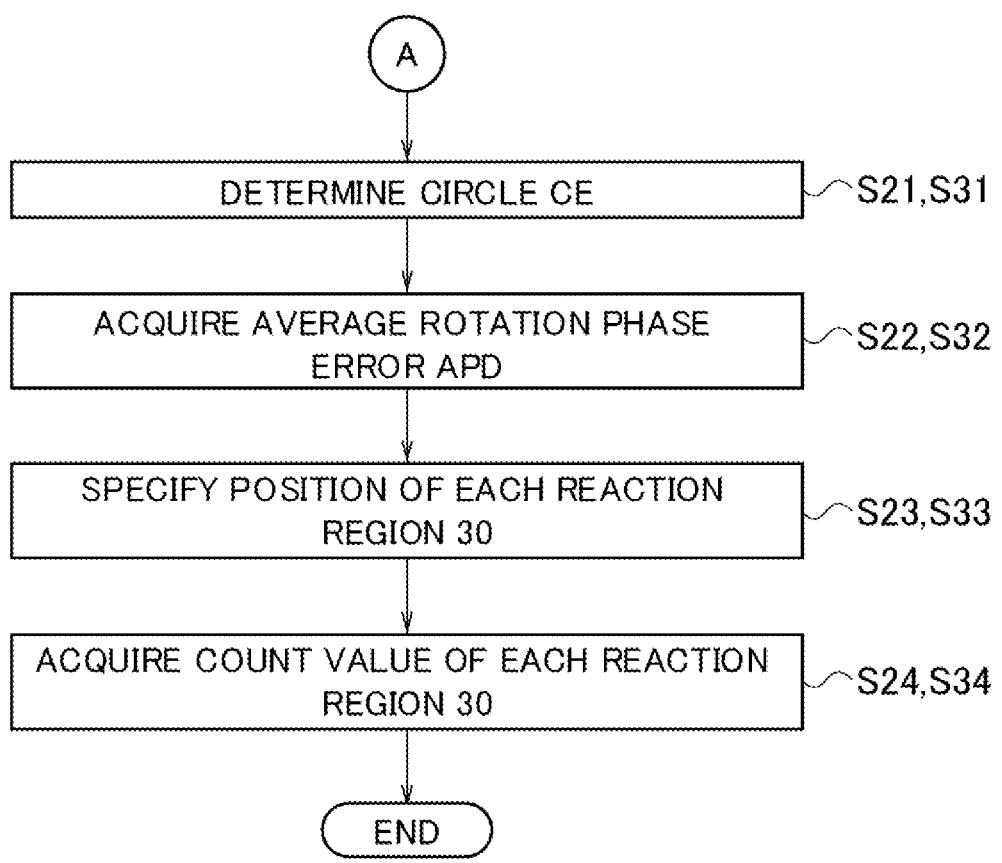
FIG. 3B is a flowchart showing an example of an analysis method of an embodiment.

In step S21 of FIG. 3B, the reaction region position coordinate computation unit 14 acquires a determination result JR from the reaction region position determination unit 15. Further, the reaction region position coordinate computation unit 14 acquires, from the determination result JR, central coordinates C30a, C30d, and C30f of the reference reaction region 30a, 30d, and 30f (the first reaction regions). Further, the reaction region position coordinate computation unit 14 determines the circle CE as a precise circle passing individual centers of the reaction regions 30a, 30d, and 30f, for example, from the central coordinates C30a, C30d, and C30f. In other words, the reaction regions 30a, 30d, and 30f are disposed such that the individual centers thereof are positioned on the circle CE as the precise circle. Further, the reaction region position coordinate computation unit 14 calculates a center point CEC of the circle CE.

In step S22, the reaction region position coordinate computation unit 14 calculates a rotation phase error PDa of the reaction regions 30a, a rotation phase error PDd of the reaction regions 30d, and a rotation phase error PDf of the reaction regions 30f. The rotation phase error PDa is a phase difference in the rotational direction from a phase reference PRa to, for example, the center of the reaction regions 30a. The phase reference PRa can be set in any manner.

A phase difference in the rotational direction from the phase reference PRa to a phase reference PRd can be calculated by a relational expression $\frac{3}{8}$ (n=8)×2π. The "n" is the number of reaction regions 30 formed on the analysis substrate 20. The rotation phase error PDd is a phase difference in the rotational direction from the phase reference PRd to, for example, the center of the reaction region 30d. A phase difference in the rotational direction from the phase reference PRa to a phase reference PRf can be calculated by a relational expression ⅝ (n=8)×2π. The rotation phase error PDf is a phase difference in the rotational direction from the phase reference PRf to, for example, the center of the reaction region 30f. Further, the reaction region position coordinate computation unit 14 calculates, for example, an average value of the rotation phase errors PDa, PDd, and PDf to acquire an average rotation phase error APD.

In step S23, the reaction region position coordinate computation unit 14 specifies positions of reaction regions 30b, 30c, 30e, 30g, and 30h (second reaction regions) other than the reference reaction regions 30a, 30d, and 30f. Specifically, the reaction region position coordinate computation unit 14 calculates a central coordinate C30b when the center of the reaction regions 30b is located on the circle CE, based on the phase reference PRb and the average rotation phase error APD. Similarly, the reaction region position coordinate computation unit 14 calculates central coordinates C30c, C30e, C30g, and C30h when the individual centers of the reaction regions 30c, 30e, 30g, and 30h are located on the circle CE, based on the phase references PRc, PRe, PRg, and PRh, and the average rotation phase error APD. In other words, the reaction region position coordinate computation unit 14 can specify positions of all the reaction regions based on the circumference of the circle CE passing the individual center positions of the selected first reaction regions, and the individual center positions of the first reaction regions.

Further, the reaction region position coordinate computation unit 14 can specify positions (ranges) of the reaction regions 30a to 30h based on the central coordinates C30a to C30h, and a design radius (or a diameter) of the reaction regions 30. Further, the reaction region position coordinate computation unit 14 outputs, to the reaction region count value computation unit 16, position information CF of the reaction regions 30a to 30h, and the table data TCD. The position information CF includes a design radius (or a diameter) of the reaction regions 30, and central coordinates C30a to C30h.

In step S24, the reaction region count value computation unit 16 specifies count values corresponding to the reaction regions 30a to 30h from the table data TCD based on the position information CF, and combines a count value for each of the reaction regions 30. This enables the analysis device 1 to calculate the count value for each of the reaction regions 30. The analysis device 1 may output the total of a count value for each of the reaction regions 30 to a display device or the like. If four or more reaction regions 30 are selected as the reference reaction regions 30, the count value for each of the reaction regions 30 can be calculated by the same procedure.

A case will be described below in which the reaction region position determination unit 15 selects the two reaction regions 30a and 30d, as the reference reaction regions 30 in step S12. In step S31 of FIG. 3B, the reaction region position coordinate computation unit 14 acquires the determination result JR from the reaction region position determination unit 15. Further, the reaction region position coordinate computation unit 14 acquires, from the determination result JR, the central coordinates C30a and C30d of the reference reaction regions 30a and 30d (the first reaction regions). Further, the reaction region position coordinate computation unit 14 determines, for example, the circle CE passing the individual centers of the reaction regions 30a and 30d, for example, by fitting the circumference of the circle CE of a preset size to the individual center positions of the central coordinates C30a and C30d.

The radius (or the diameter) of the circle CE is preset. Therefore, the circle CE passing the individual centers of the reaction regions 30a and 30d can be determined based on the central coordinates C30a and C30d, and the radius of the circle CE. In other words, the reaction regions 30a and 30d are disposed such that the individual centers thereof are located on the circle CE. Further, the reaction region position coordinate computation unit 14 calculates the center point CEC of the circle CE.

In step S32, the reaction region position coordinate computation unit 14 calculates the rotation phase error PDa of the reaction regions 30a and the rotation phase error PDd of the reaction regions 30d. Further, the reaction region position coordinate computation unit 14 calculates, for example, an average value of the rotation phase errors PDa and PDd to acquire the average rotation phase error APD.

In step S33, the reaction region position coordinate computation unit 14 specifies positions of the reaction regions 30b, 30c and 30e to 30h (second reaction regions) other than the reference reaction region 30a and 30d. The positions of the reaction regions 30b, 30c, and 30e to 30h (the central coordinates C30b, C30c, and C30e to C30h) can be identified by the same procedure as in step S23. That is, the reaction region position coordinate computation unit 14 can specify the positions of all the reaction regions based on the circumference of the circle CE determined in step S31 and the individual center positions of the first reaction regions. Further, the reaction region position coordinate computation unit 14 outputs, to the reaction region count value computation unit 16, the position information CF of the reaction regions 30a to 30h, and the table data TCD.

In step S34, the reaction region count value computation unit 16 specifies the count values corresponding to the reaction regions 30a to 30h from the table data TCD based on the position information CF, and combines a count value for each of the reaction regions 30. This enables the analysis device 1 to acquire only the count value for each of the reaction regions 30. The analysis device 1 may output the total of a count value for each of the reaction regions 30 to a display device or the like.

In the analysis device 1 and the analysis method of the present embodiment, the table data TCD is generated, the position of each of the reaction regions 30 is estimated based on the table data TCD, and the reference reaction region 30 is selected. Furthermore, in the analysis device 1 and the analysis method of the present embodiment, the circle CE in which all the reaction regions 30 are arranged is determined based on the reference reaction region 30, the position of each of the reaction regions 30 is specified based on the rotation phase error PD, and the count values corresponding to the specified reaction regions 30 are specified. Accordingly, only the count values in a range corresponding to the reaction regions 30 can be acquired from the table data TCD.

In the analysis device and the analysis method of the present embodiment, the shape of each of the reaction regions 30 has been described as a circle having a predetermined radius. However, the shape of each of the reaction regions 30 is not limited to a circle, but may be any shape as long as the center of a shape can be specified.

Therefore, an analysis device 1 and the analysis method of the present embodiment can suppress the deterioration in the analysis accuracy, because even if the reaction region 30 is formed at a position deviated from a target position on the analysis substrate 20, only a count value of the reaction region 30 at the deviated position can be extracted.

The present invention is not limited to the above-described embodiments, and various modifications can be made without departing from the scope of the present invention.

What is claimed is:

1. An analysis device using an analysis substrate on which a plurality of reaction regions are formed by a fine particle for labeling a detection target substance being fixed to the detection target substance captured on a track, the analysis device comprising:
   an optical pickup that receives reflected light obtained by irradiating the analysis substrate with a laser beam, and generates a light reception level signal; and
   a controller, wherein the controller is configured to:
   generate gate signals for each of a plurality of the tracks within a measurement range preset on the analysis substrate, the gate signals corresponding to a plurality of divided measurement ranges obtained by dividing each of the tracks in a circumferential direction, extract a fine particle pulse signal from the light reception level signal by using the gate signals, count a pulse number for each of the gate signals from the extracted fine particle pulse signals, and output a count value for each of the divided measurement ranges;
   generate count value in-plane distribution data in the measurement range based on the count value;
   estimate positions of all the reaction regions based on the count value in-plane distribution data;
   select two first reaction regions from all the estimated reaction regions, and fit a circumference of a precise circle with a predetermined size to individual center positions of the two first reaction regions, so that the positions of all the reaction regions are specified based on the circumference and the individual center positions of the two first reaction regions; and
   calculate the count value for each of all the specified reaction regions.

2. An analysis device using an analysis substrate on which a plurality of reaction regions are formed by a fine particle for labeling a detection target substance being fixed to the detection target substance captured on a track, the analysis device comprising:
   an optical pickup that receives reflected light obtained by irradiating the analysis substrate with a laser beam, and generates a light reception level signal; and
   a controller, the controller being configured to:
   generate gate signals for each of a plurality of the tracks within a measurement range preset on the analysis substrate, the gate signals corresponding to a plurality of divided measurement ranges obtained by dividing each of the tracks in a circumferential direction, extract a fine particle pulse signal from the light reception level signal by using the gate signals, count a pulse number for each of the gate signals from the extracted fine particle pulse signals, and output a count value for each of the divided measurement ranges;
   generate count value in-plane distribution data in the measurement range based on the count value;
   estimate positions of all the reaction regions based on the count value in-plane distribution data;
   select three first reaction regions from all the reaction regions estimated, and specify the positions of all the reaction regions based on the circumference of the precise circle passing the individual center position of the selected three first reaction regions and the individual center position of the three first reaction regions; and
   calculate the count value for each of all the specified reaction regions.

3. An analysis method comprising:
   receiving, by an optical pickup, reflected light obtained by irradiating an analysis substrate with a laser beam, and generating a light reception level signal, the analysis substrate being formed with a plurality of reaction regions by a fine particle for labeling a detection target substance being fixed to the detection target substance captured on a track,
   generating, by a controller, gate signals for each of a plurality of the tracks within a measurement range preset on the analysis substrate, the gate signals corresponding to a plurality of divided measurement ranges obtained by dividing each of the tracks in a circumferential direction, extracting a fine particle pulse signal from the light reception level signal by using the gate signals, counting a pulse number for each of the gate signals from the extracted fine particle pulse signal, and outputting a count value for each of the divided measurement ranges;
   generating, by the controller, count value in-plane distribution data in the measurement range, based on the count value output from the signal processing circuit;
   estimating, by the controller, positions of all the reaction regions based on the count value in-plane distribution data;
   selecting two first reaction regions from all the estimated reaction regions, and fitting a circumference of a precise circle with a predetermined size to individual center positions of the two first reaction regions, so that the positions of all the reaction regions are specified based on the circumference and the individual center positions of the two first reaction regions; and
   calculating, by the controller, the count value for each of all the specified reaction regions.

4. An analysis method comprising:
   receiving, by an optical pickup, reflected light obtained by irradiating an analysis substrate with a laser beam, and generating a light reception level signal, the analysis substrate being formed with a plurality of reaction regions by a fine particle for labeling a detection target substance being fixed to the detection target substance captured on a track,
   generating, by a controller, gate signals for each of a plurality of the tracks within a measurement range preset on the analysis substrate, the gate signals corresponding to a plurality of divided measurement ranges obtained by dividing each of the tracks in a circumferential direction, extracting a fine particle pulse signal from the light reception level signal by using the gate signals, counting a pulse number for each of the gate signals from the extracted fine particle pulse signal, and outputting a count value for each of the divided measurement ranges;
   generating, by the controller, count value in-plane distribution data in the measurement range, based on the count value;
   estimating, by the controller, positions of all the reaction regions based on the count value in-plane distribution data; and
   selecting two first reaction regions from all the estimated reaction regions, and fitting a circumference of a precise circle with a predetermined size to individual center positions of the two first reaction regions, so that the positions of all the reaction regions are specified based on the circumference and the individual center positions of the first reaction regions; and calculating, by the controller, the count value for each of all the specified reaction regions.

\* \* \* \* \*

UNITED STATES PATENT AND TRADEMARK OFFICE
CERTIFICATE OF CORRECTION

| | | |
|---|---|---|
| PATENT NO. | : 12,007,325 B2 | |
| APPLICATION NO. | : 17/477685 | |
| DATED | : June 11, 2024 | |
| INVENTOR(S) | : Atsushi Saito and Makoto Itonaga | |

It is certified that error appears in the above-identified patent and that said Letters Patent is hereby corrected as shown below:

On the Title Page

Item (73) Assignee, please add the Assignee city and country as "Yokohama (JP)".

Signed and Sealed this
Sixteenth Day of July, 2024

Katherine Kelly Vidal
*Director of the United States Patent and Trademark Office*